(12) United States Patent  
Schwartz et al.

(10) Patent No.: US 9,289,201 B2  
(45) Date of Patent: Mar. 22, 2016

(54) MEDICAL DEVICE FOR REPAIR OF TISSUE AND METHOD FOR IMPLANTATION AND FIXATION

(75) Inventors: Herbert Eugene Schwartz, Fort Wayne, IN (US); Francis S. Proch, Huntertown, IN (US)

(73) Assignee: Howmedica Osteonics Corp., Mahwah, NJ (US)

( * ) Notice: Subject to any disclaimer, the term of this patent is extended or adjusted under 35 U.S.C. 154(b) by 942 days.

(21) Appl. No.: 12/310,059

(22) PCT Filed: Aug. 6, 2007

(86) PCT No.: PCT/US2007/075236  
§ 371 (c)(1),  
(2), (4) Date: Oct. 20, 2009

(87) PCT Pub. No.: WO2008/021770  
PCT Pub. Date: Feb. 21, 2008

(65) Prior Publication Data  
US 2010/0036389 A1 Feb. 11, 2010

Related U.S. Application Data

(63) Continuation of application No. 11/462,728, filed on Aug. 7, 2006, now abandoned.

(51) Int. Cl.  
*A61B 17/04* (2006.01)  
*A61B 17/064* (2006.01)

(52) U.S. Cl.  
CPC .......... *A61B 17/0401* (2013.01); *A61B 17/0469* (2013.01); *A61B 17/064* (2013.01);  
(Continued)

(58) Field of Classification Search  
CPC ................... A61B 17/0401; A61B 2017/0646; A61B 2017/0648; A61B 2017/0464; A61B 2017/0404; A61B 2017/0403

USPC ............. 606/139, 151, 232; 623/13.11, 23.72  
See application file for complete search history.

(56) References Cited

U.S. PATENT DOCUMENTS 4,484,570 A 11/1984 Sutter et al.  
4,884,572 A 12/1989 Bays et al.  
(Continued)

FOREIGN PATENT DOCUMENTS

CA 1292596 12/1991  
CA 2155422 8/1994  
(Continued)

OTHER PUBLICATIONS

Australian Examination Report for Application No. 2007284135 dated Sep. 9, 2013.  
(Continued)

*Primary Examiner* — Alexander Orkin  
(74) *Attorney, Agent, or Firm* — Lerner, David, Littenberg, Krumholz & Mentlik, LLP

(57) ABSTRACT

The present invention relates to medical devices for repairing tissue and more specifically to devices which facilitate tissue regeneration and to surgical methods for the implantation and fixation of such devices. In one embodiment, the medical device is an elongate conduit that includes a longitudinal bore extending therethrough to facilitate the transfer of blood from a vascular region of tissue to a tear or damaged area located in an avascular and/or semi-vascular region of tissue. A filament and/or filaments are attached to the conduit and are positioned to secure the conduit and fixate the adjacent tear walls in mutual engagement. In another embodiment, a series of conduits are connected via a filament and/or filaments to facilitate the implantation of multiple conduits.

18 Claims, 12 Drawing Sheets

(52) U.S. Cl.
CPC ....... *A61B17/0487* (2013.01); *A61B 2017/044* (2013.01); *A61B 2017/0458* (2013.01); *A61B 2017/0459* (2013.01); *A61B 2017/0464* (2013.01); *A61B 2017/0475* (2013.01); *A61B 2017/0496* (2013.01); *A61B 2017/0646* (2013.01); *A61B 2017/0648* (2013.01)

(56) References Cited

U.S. PATENT DOCUMENTS

| | | | |
|---|---|---|---|
| 4,968,317 A | 11/1990 | Tormala et al. | |
| 4,976,715 A | 12/1990 | Bays et al. | |
| 5,041,129 A | 8/1991 | Hayhurst et al. | |
| 5,059,206 A | 10/1991 | Winters | |
| 5,085,629 A | 2/1992 | Goldberg et al. | |
| 5,129,906 A | 7/1992 | Ross et al. | |
| 5,152,790 A | 10/1992 | Rosenberg et al. | |
| 5,152,791 A | 10/1992 | Hakamatsuka et al. | |
| 5,236,431 A | 8/1993 | Gogolewski et al. | |
| 5,261,914 A | 11/1993 | Warren | |
| 5,269,809 A | 12/1993 | Hayhurst et al. | |
| 5,370,662 A | 12/1994 | Stone et al. | |
| 5,374,268 A | 12/1994 | Sander | |
| 5,403,348 A | 4/1995 | Bonutti | |
| 5,470,337 A | 11/1995 | Moss | |
| 5,500,000 A | 3/1996 | Feagin et al. | |
| 5,503,634 A | 4/1996 | Christy | |
| 5,522,843 A | 6/1996 | Zang | |
| 5,569,252 A | 10/1996 | Justin et al. | |
| 5,669,909 A | 9/1997 | Zdeblick et al. | |
| 5,681,353 A | 10/1997 | Li et al. | |
| 5,683,366 A | 11/1997 | Eggers et al. | |
| 5,702,462 A | 12/1997 | Oberlander | |
| 5,725,549 A | 3/1998 | Lam | |
| 5,730,744 A | 3/1998 | Justin et al. | |
| 5,782,866 A | 7/1998 | Wenstrom, Jr. | |
| 5,824,011 A | 10/1998 | Stone et al. | |
| 5,842,477 A | 12/1998 | Naughton et al. | |
| 5,871,475 A | 2/1999 | Frassica | |
| 5,873,855 A | 2/1999 | Eggers et al. | |
| 5,899,917 A | 5/1999 | Edwards et al. | |
| 5,935,119 A | 8/1999 | Guy et al. | |
| 5,954,747 A | 9/1999 | Clark | |
| 5,976,127 A | 11/1999 | Lax | |
| 5,980,559 A | 11/1999 | Bonutti | |
| 6,039,753 A * | 3/2000 | Meislin | 606/213 |
| 6,045,551 A * | 4/2000 | Bonutti | 606/60 |
| 6,056,778 A | 5/2000 | Grafton et al. | |
| 6,068,648 A | 5/2000 | Cole et al. | |
| 6,096,060 A | 8/2000 | Fitts et al. | |
| 6,102,046 A | 8/2000 | Weinstein et al. | |
| 6,146,387 A | 11/2000 | Trott et al. | |
| 6,203,556 B1 | 3/2001 | Evans et al. | |
| 6,270,517 B1 * | 8/2001 | Brotz | 606/228 |
| 6,290,728 B1 | 9/2001 | Phelps et al. | |
| 6,306,156 B1 | 10/2001 | Clark | |
| 6,306,159 B1 | 10/2001 | Schwartz et al. | |
| 6,319,270 B1 | 11/2001 | Grafton et al. | |
| 6,319,271 B1 | 11/2001 | Schwartz et al. | |
| 6,338,739 B1 | 1/2002 | Datta et al. | |
| 6,387,111 B1 * | 5/2002 | Barber | 606/184 |
| 6,468,277 B1 | 10/2002 | Justin et al. | |
| 6,503,251 B1 | 1/2003 | Shadduck | |
| 6,511,958 B1 | 1/2003 | Atkinson et al. | |
| 6,514,514 B1 | 2/2003 | Atkinson et al. | |
| 6,517,542 B1 | 2/2003 | Papay et al. | |
| 6,548,569 B1 | 4/2003 | Williams et al. | |
| 6,569,191 B1 | 5/2003 | Hogan | |
| 6,595,990 B1 | 7/2003 | Weinstein et al. | |
| 6,638,237 B1 | 10/2003 | Guiles et al. | |
| 6,660,008 B1 | 12/2003 | Foerster et al. | |
| 6,685,695 B2 | 2/2004 | Ferree | |
| 6,685,728 B2 | 2/2004 | Sinnott et al. | |
| 6,692,499 B2 | 2/2004 | Tormala et al. | |
| 6,695,499 B2 | 2/2004 | Bartolome et al. | |
| 6,763,836 B2 | 7/2004 | Tasto et al. | |
| 6,780,164 B2 | 8/2004 | Bergheim et al. | |
| 6,838,493 B2 | 1/2005 | Williams et al. | |
| 6,867,247 B2 | 3/2005 | Williams et al. | |
| 6,884,428 B2 | 4/2005 | Binette et al. | |
| 6,932,834 B2 | 8/2005 | Lizardi et al. | |
| 6,972,027 B2 | 12/2005 | Fallin et al. | |
| 7,153,312 B1 | 12/2006 | Torrie et al. | |
| 7,163,563 B2 | 1/2007 | Schwartz et al. | |
| 7,588,587 B2 | 9/2009 | Barbieri et al. | |
| 7,608,098 B1 | 10/2009 | Stone et al. | |
| 2002/0068930 A1 | 6/2002 | Tasto et al. | |
| 2002/0169477 A1 | 11/2002 | Demopulos et al. | |
| 2003/0078600 A1 | 4/2003 | O'Quinn et al. | |
| 2003/0097148 A1 | 5/2003 | Valimaa et al. | |
| 2003/0100859 A1 | 5/2003 | Henderson et al. | |
| 2003/0144696 A1 | 7/2003 | Sinnott et al. | |
| 2004/0064081 A1 | 4/2004 | Stanish | |
| 2004/0093032 A1 | 5/2004 | Sinnott et al. | |
| 2004/0138683 A1 | 7/2004 | Shelton et al. | |
| 2004/0230195 A1 | 11/2004 | Kaikkonen et al. | |
| 2004/0260343 A1 | 12/2004 | Leclair | |
| 2005/0033363 A1 | 2/2005 | Bojarski et al. | |
| 2005/0234549 A1 | 10/2005 | Kladakis et al. | |
| 2005/0246023 A1 | 11/2005 | Yeung | |
| 2005/0271704 A1 | 12/2005 | Tu et al. | |
| 2006/0089646 A1 | 4/2006 | Bonutti | |
| 2006/0100627 A1 | 5/2006 | Stone et al. | |
| 2006/0189993 A1 | 8/2006 | Stone | |
| 2006/0190042 A1 | 8/2006 | Stone et al. | |
| 2006/0247600 A1 | 11/2006 | Yeung et al. | |
| 2006/0247642 A1 | 11/2006 | Stone et al. | |
| 2006/0280768 A1 | 12/2006 | Hwang et al. | |
| 2006/0282085 A1 | 12/2006 | Stone et al. | |
| 2007/0067025 A1 | 3/2007 | Schwartz | |
| 2007/0185532 A1 | 8/2007 | Stone et al. | |
| 2007/0185568 A1 | 8/2007 | Schwartz | |
| 2008/0027446 A1 | 1/2008 | Stone et al. | |
| 2008/0033487 A1 | 2/2008 | Schwartz et al. | |
| 2008/0065114 A1 | 3/2008 | Stone et al. | |
| 2008/0082128 A1 | 4/2008 | Stone | |
| 2008/0132932 A1 | 6/2008 | Hoeppner et al. | |
| 2008/0140092 A1 | 6/2008 | Stone et al. | |
| 2008/0140093 A1 | 6/2008 | Stone et al. | |
| 2008/0146918 A1 | 6/2008 | Magnin et al. | |
| 2008/0255613 A1 | 10/2008 | Kaiser et al. | |
| 2008/0312689 A1 | 12/2008 | Denham et al. | |
| 2009/0018561 A1 | 1/2009 | Schwartz et al. | |

FOREIGN PATENT DOCUMENTS

| | | |
|---|---|---|
| CA | 2168835 | 8/1996 |
| JP | 03-178652 | 8/1991 |
| JP | 2004-000540 | 1/2004 |
| WO | 93/15694 | 8/1993 |
| WO | 97/32551 | 9/1997 |
| WO | 99/21510 | 5/1999 |
| WO | 00/36997 | 6/2000 |
| WO | 03/007784 | 1/2003 |
| WO | 03063713 A1 | 8/2003 |
| WO | 2005104992 | 11/2005 |
| WO | 2006055516 A2 | 5/2006 |

OTHER PUBLICATIONS

Smith & Nephew Technique Plus Illustrated Guide—Meniscal Repair with the FasT-Fix Suture System.
Adams et at., J. of Knee Surgery, Tissue Engineering for Meniscus Repair, vol. 18(1), 2005, pp. 25-30.
Amoczky et aL., J. of Bone and Joint Surgery, Meniscal Repair Using an Exogenous Fibrin Clot, vol. 70A(8), 1988, pp. 1200-1217.
Fox et al, J. of Arthroscopic and Related Surgery, Treytination of Incomplegte Meniscal Tears,9(4), 1993, pp. 451-455.
Okuda et aL., J of Arthroscopic and Related Surgery, Meniscal Rasping for Repair of Meniscal Tear in the Avascular Zone, vol. 15(3),1999, pp. 281-286.
O'Meara, p., Orthopaedic Review, The Basic Science of Meniscus Repair, Jun. 1993, pp. 681-686.

(56) References Cited

OTHER PUBLICATIONS

Sgaglione et at., J. of Arthroscopic and Related Surgery, Current Concpets in Meniscus Surgery Resection to Replacement, vol. 19(10), 2003, pp. 161-188.

Zhang et at., Am. J. of Sports Medidne, Repairs by Trephination and Suturing of Longitudinal Injuries in the Avascular Area of the Meniscus in Goats, vol. 23(1), 1995, pp. 35-41.

Supplementary European Search Report issued on Jul. 28, 2008 in connection with corresponding European Application No. EP 05 73 9944.

U.S. Appl. No. 10/983,236.

U.S. Appl. No. 10/984,624.

European Search Report for Application No. EP07800009.8 dated Feb. 12, 2015.

* cited by examiner

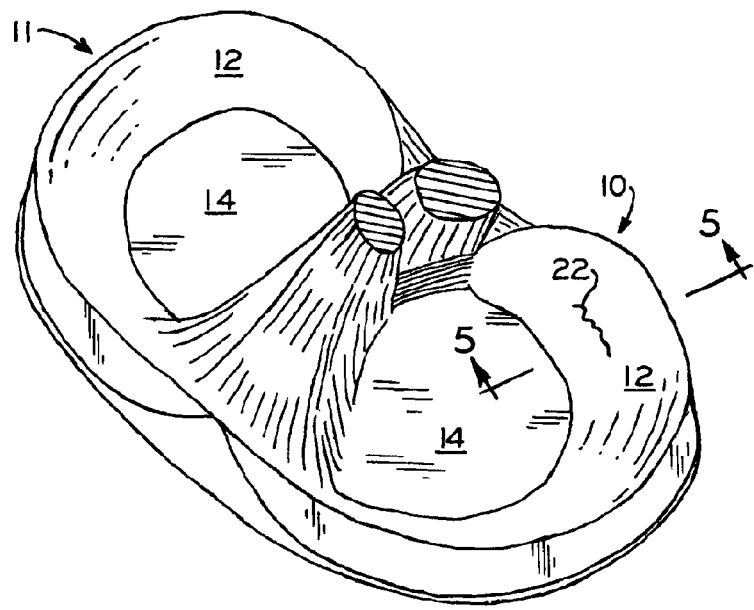
FIG_3
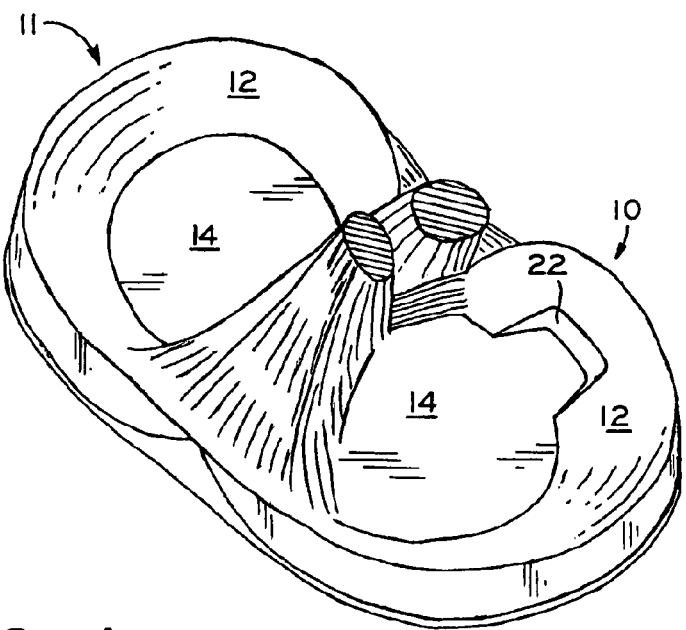
FIG_4

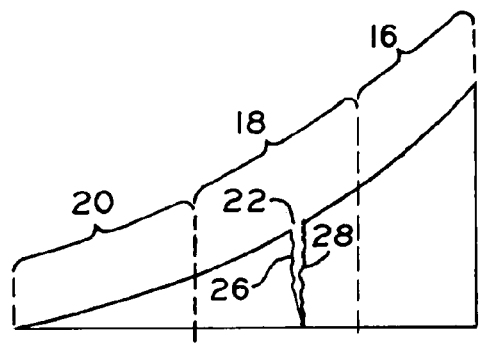
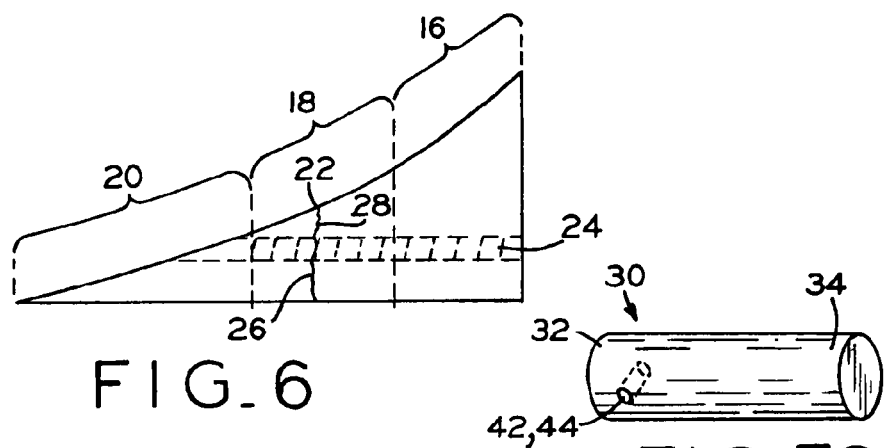
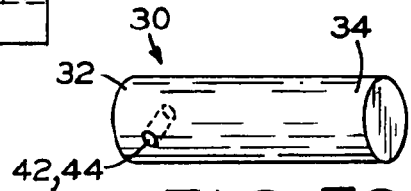
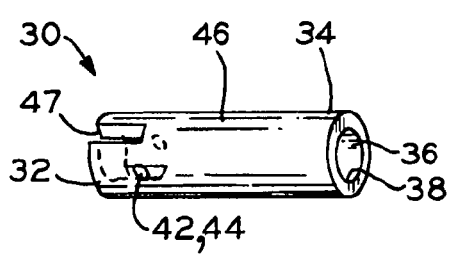
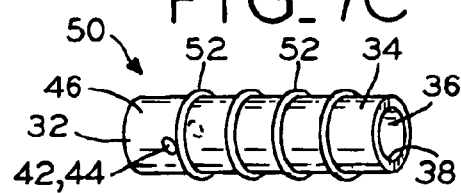
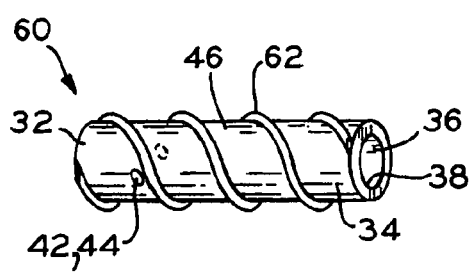
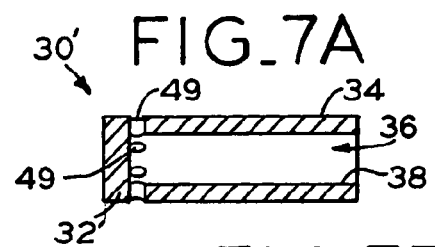
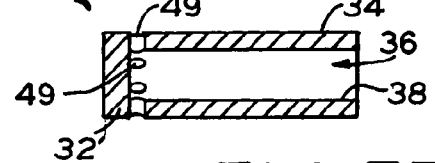

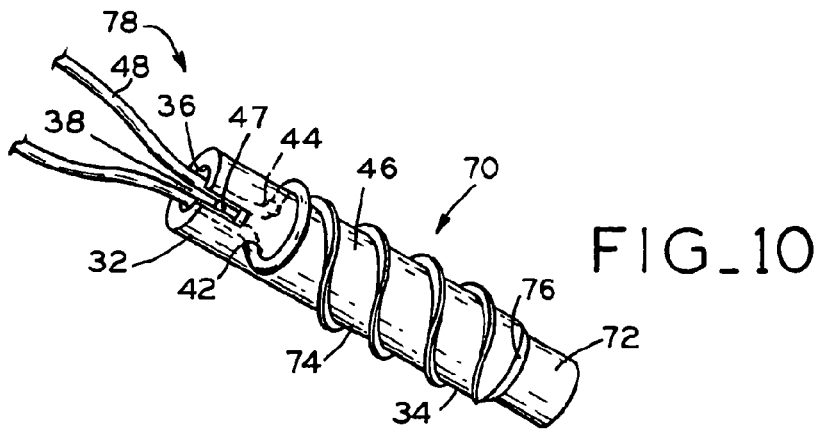
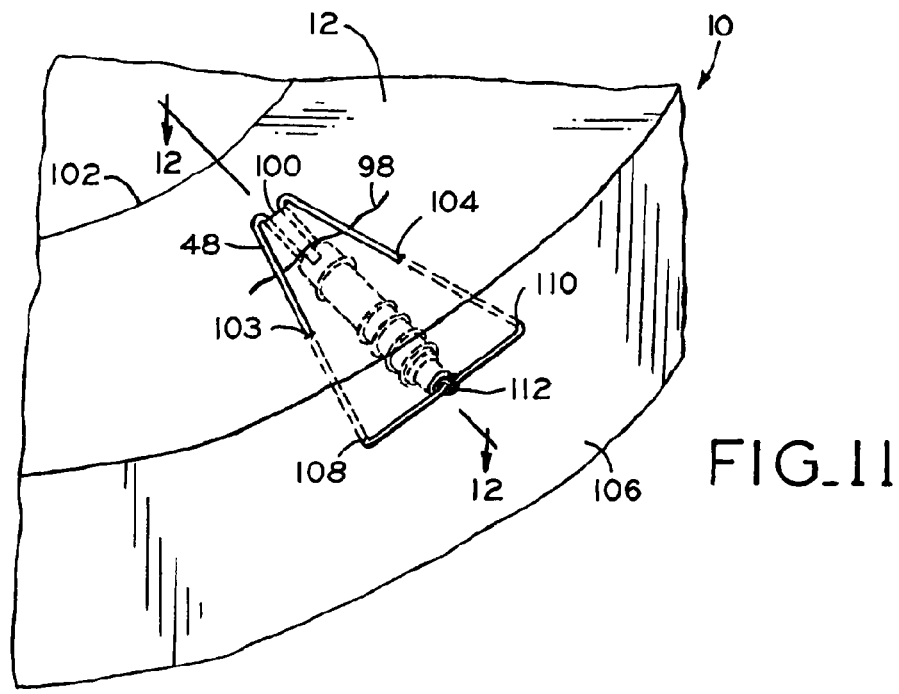
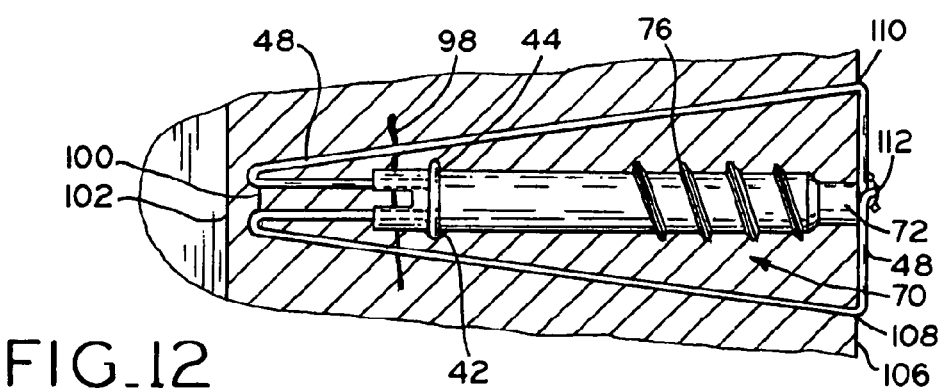

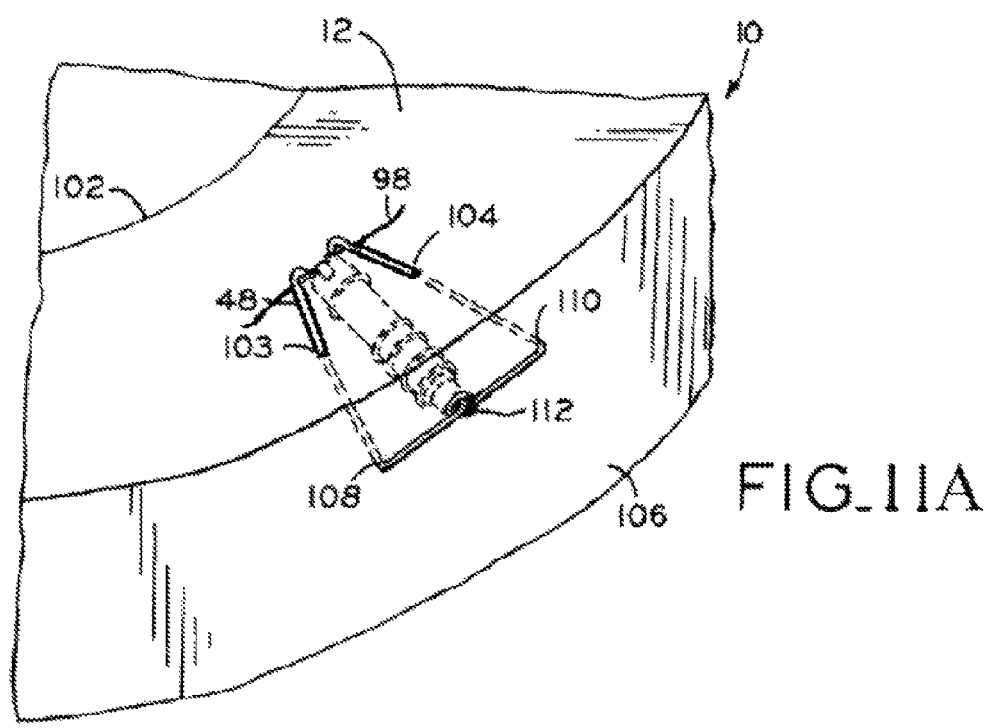
FIG_11A

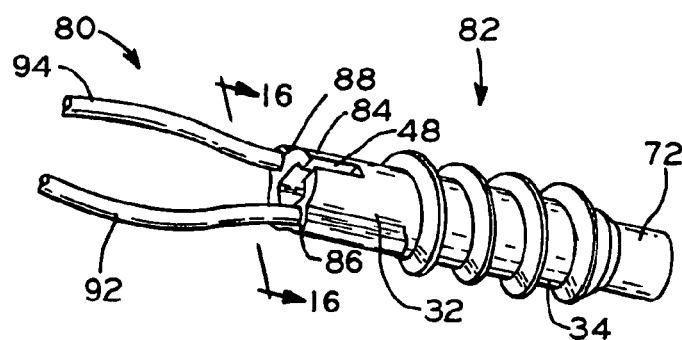
FIG_15
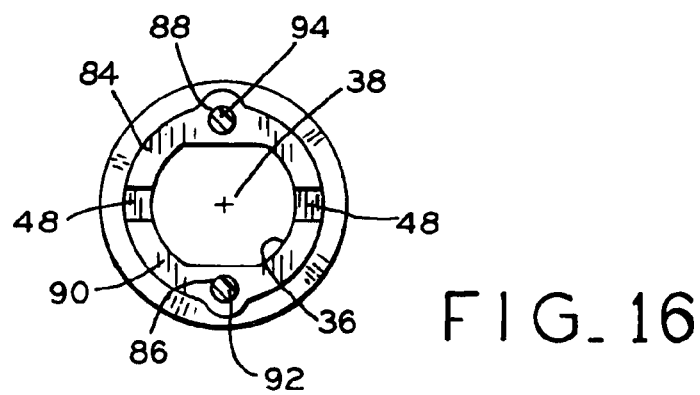
FIG_16

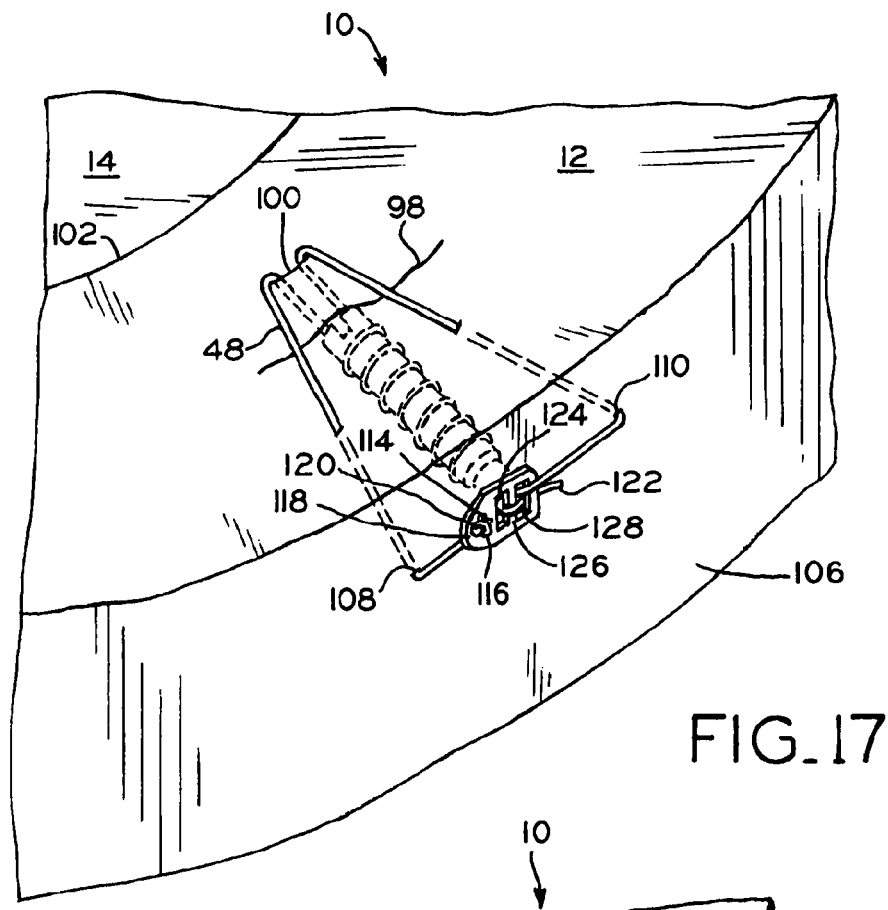
FIG_17
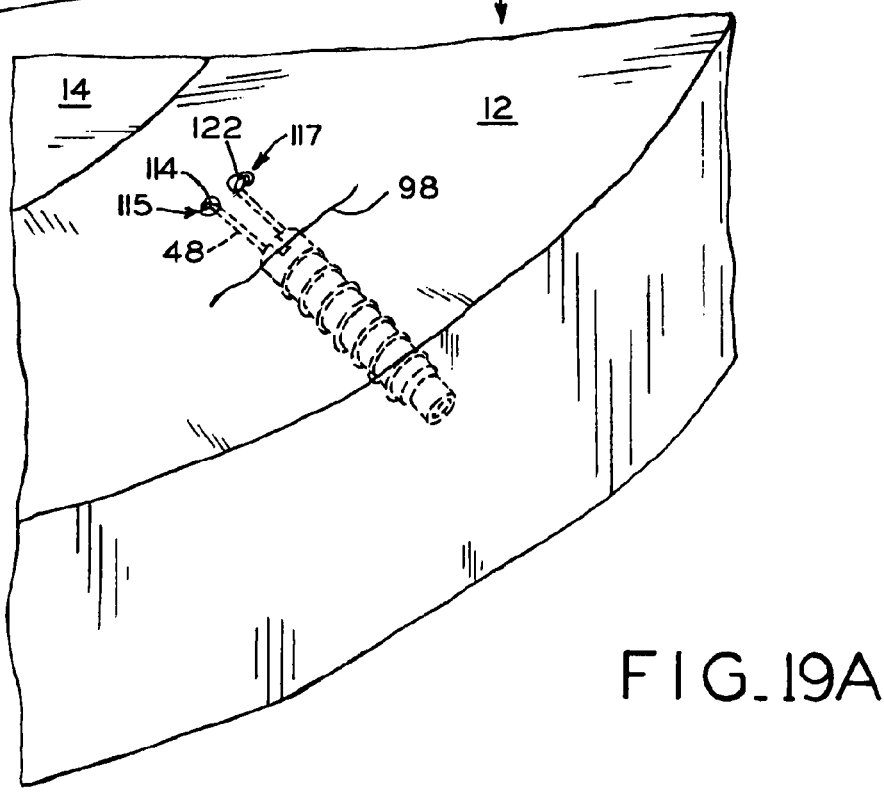
FIG_19A

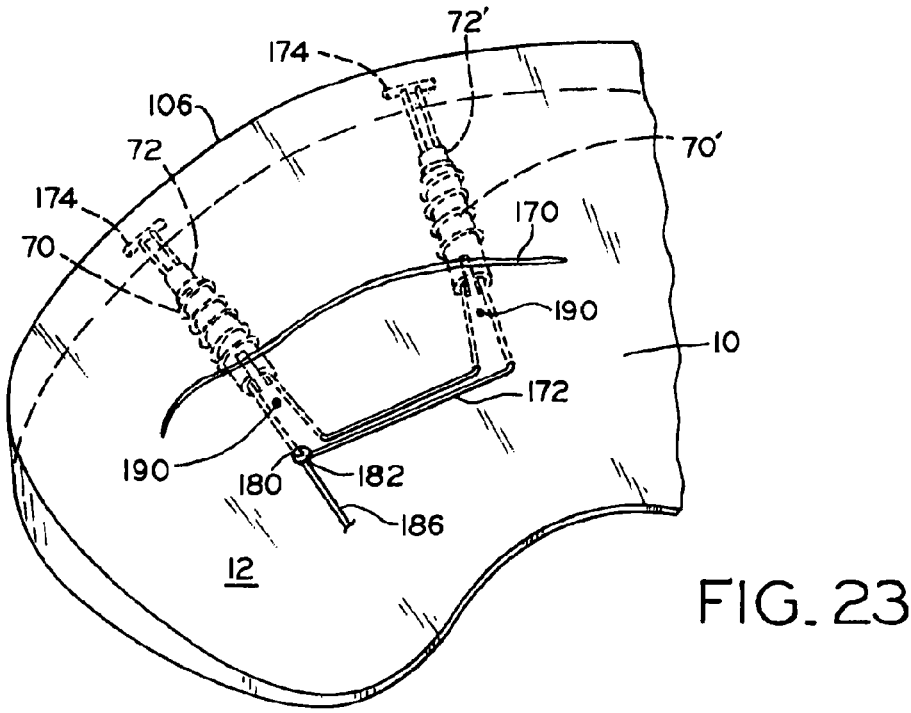
FIG. 23
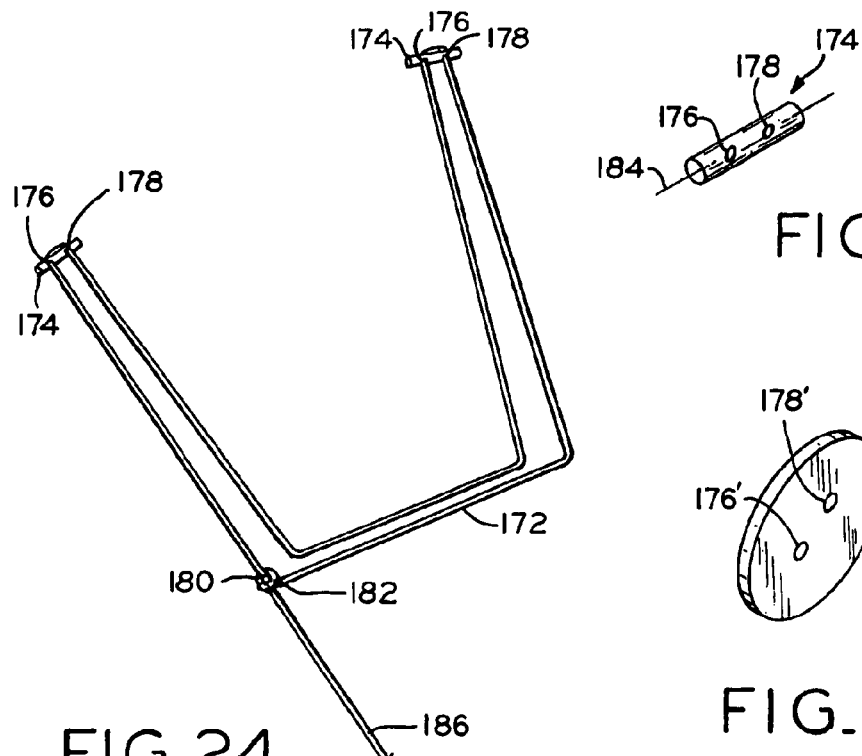
FIG. 24
FIG. 25
FIG. 26

MEDICAL DEVICE FOR REPAIR OF TISSUE AND METHOD FOR IMPLANTATION AND FIXATION

CROSS-REFERENCE TO RELATED APPLICATIONS

The present application is a national phase entry under 35 U.S.C. §371 of International Application No. PCT/US2007/075236 filed Aug. 6, 2007, published in English, which is a continuation of U.S. application Ser. No. 11/462,728 filed Aug. 7, 2006, all of which are incorporated herein by reference.

BACKGROUND OF THE INVENTION

1. Field of the Invention

The present invention relates to medical devices for repairing tissue and more specifically to devices which facilitate tissue regeneration and to surgical methods for the implantation and fixation thereof.

2. Description of the Related Art

Various parts of the human body are comprised of fibrocartilage. Fibrocartilage forms the disc, meniscus, and labrums, located in the spine and temporo-mandibular joint, knee, and shoulder and hip, respectively. Additionally, fibrocartilage is present in other parts of the human body, such as fingers, wrists, and ankles. Fibrocartilage is a resilient, compressive tissue capable of accepting and withstanding high loads imparted during bodily movement. Generally, fibrocartilage is found between two adjacent bones, such as the locations set forth hereinabove.

The fibrocartilage of the knee forms menisci 10, 11, shown in FIG. 1. Menisci 10, 11 are semi-lunar, wedge-shaped portions of tissue that sit atop the tibia and articulate with the tibia and femur during movement of the tibia and/or femur relative to one another. Menisci 10, 11 have top articulating surfaces 12 which interface with the femoral condyle and bottom articulating surfaces (not shown) which interface with tibia plateau 14. Menisci 10, 11 function as shock absorbers between the femur and the tibia to distribute compressive and shear loads from the curved condyles of the femur to the relatively flat plateau of the tibia. While much of menisci 10, 11 can be classified as avascular and aneural, each menisci 10, 11 has three distinct zones of vascularity, shown in FIG. 2, red zone 16, red/white zone 18, and white zone 20. Red zone 16, comprised of approximately the outer peripheral third of each meniscus, is rich in blood supply and is highly vascular. White zone 20, comprised of approximately the inner peripheral third of each meniscus, is completely void of blood supply and is avascular. Red/white zone 18, comprised of the area between the red zone and white zone, has some limited vascularity with limited blood supply. As a patient ages, the size of the white zone 20 will increase and the size of red zone 16 and red/white zone 18 will correspondingly decrease.

Due to the high stress imparted on fibrocartilage, injuries and pathologies can occur in the fibrocartilage which are manifested in the form of tears, such as tear 22 shown in FIG. 3, defects, and/or degeneration. Tears may occur due to the existence of prior defects in the fibrocartilage, shear loading of the fibrocartilage, and/or compounded loading resulting from repetitive compressive loading occurring over a period of time. Additionally, fibrocartilage can deteriorate as a result of aging, resulting in hard and/or soft areas which further facilitate the creation of tears therein.

One common procedure for treating fibrocartilage tears is to surgically remove part or all of the fibrocartilage surrounding the tear, such as removing a portion of the meniscus. These procedures, known as meniscectomies or partial meniscectomies when performed on the meniscus, are commonly utilized in the case of "unrepairable" or complex tears such as radial tears, horizontal tears, and vertical longitudinal tears occurring outside the vascular zone. Additionally, these procedures may be performed when there is fibrillation and/or degeneration caused by defects in an avascular or limited vascular area, since these injuries are unlikely to heal. As shown in FIG. 4, a partial meniscectomy may be performed in which the meniscus is removed along lines extending inwardly toward the inner meniscus from the peripheral ends of tear 22. In some cases, implants may be inserted to replace the portion of the meniscus removed during the procedure. Meniscectomies, and similar fibrocartilage procedures, typically provide immediate pain relief and restoration of knee function to a patient. However, cartilage wear on the condylar or tibial plateau surfaces and the eventual development of osteoarthritis may occur as a result of the meniscectomy. Additionally, the onset of osteoarthritis may lead to more chronic conditions resulting in the need for a total knee replacement procedure.

Another method for treating fibrocartilage tears, including tears of the meniscus, is to attempt to surgically repair the torn tissue. This technique is most commonly performed when the tear is a longitudinal vertical tear located in the vascular area of the fibrocartilage, such as red zone 16 of meniscus 10, shown in FIG. 2. To facilitate tissue regeneration, the tear walls may be rasped or trephined to induce bleeding. Additionally, the tear walls may be stabilized with sutures or other retention devices.

A further method for treating fibrocartilage tears is the subject of U.S. patent application Ser. No. 10/558,926 to Schwartz ("Schwartz '926"). The stent of Schwartz '926 is designed with an interior, longitudinally-extending bore and external threads or ribs. Stent 24, shown in FIG. 6, is inserted through fibrocartilage tissue and positioned to extend across walls 26, 28 of fibrocartilage tear 22, shown in FIG. 5, to secure the sides of the tear together. The threads or ribbing of stent 24, denoted by slanted, dashed lines in FIG. 6, effectively retain the stent, and corresponding tear walls 26, 28, in position. Additionally, the outer wall of stent 24 includes a plurality of apertures, not shown, extending from the interior of the longitudinal bore to the exterior surface of stent 24. These apertures allow for the dissemination of blood, biological factors, and cells from stent 24, as blood, biological factors, and cells flow through stent 24 from a vascular region of the fibrocartilage to a semi-vascular or avascular tear region of the fibrocartilage. The dissemination of blood, biological factors, and cells via stent 24 stimulates tissue regeneration. While the device disclosed in Schwartz '926 is effective, the walls of the fibrocartilage tear may actually be pushed apart during implantation of the stent and prevent effective healing of the tear. Additionally, even when the sides of the tear are properly aligned, the tear walls may loosen or migrate over time. Further, the blood dissemination apertures in the stent may not be as effective in providing maximum blood flow to the area of interest as desired to effect healing.

What is needed is a device that is an improvement over the prior art.

SUMMARY OF THE INVENTION

The present invention relates to medical devices for repairing tissue and more specifically to devices which facilitate tissue regeneration and to surgical methods for the implantation and fixation of such devices. In one embodiment, the medical device is an elongate conduit that includes a longitudinal bore extending therethrough to facilitate the transfer of blood, biological factors, and cells from a vascular region of tissue to a tear or damaged area located in an avascular and/or semi-vascular region of tissue. A filament and/or filaments are attached to the conduit and are positioned to fixate the adjacent tear walls in mutual engagement. In another embodiment, a series of conduits are connected via a filament and/or filaments to facilitate the implantation of multiple conduits while fixating the adjacent tear walls.

Advantageously, the present medical device allows for the provision of blood, biological factors, and cells from a vascular region of tissue to a torn or damaged area located in an avascular and/or semi-vascular region of tissue and provides for fixation of the tear walls or damaged area and the securement of a conduit in a desired position. Additionally, because the conduit itself anchors one side of the primary tear fixation, the conduit can be located with one end adjacent the plane of a tear, damaged area, or implant, allowing the conduit to efficiently deliver blood, biological factors, and cells thereto and increase the rapidity of the healing process. Moreover, in addition to facilitating the transfer of blood, biological factors, and cells from a vascular region to an avascular and/or semi-vascular region, the conduit can also provide for delivery of biological treatments, drugs, and other substances, such as blood, platelet rich plasma, growth factors, or cells, to the tear or defect area through the bore of the conduit. The desired substance can be delivered before, during, or after the conduit is inserted and positioned.

In one form thereof, the present invention provides a medical device including an elongate conduit formed of biocompatible material, the device body having an exterior, a first end, a second end, and a longitudinal bore; and a filament attached to the device body, whereby the filament can be positioned to fixate tissue in a desired position.

In another form thereof, the present invention provides a method for implanting a medical device in tissue, the tissue having a first area of vascularity and a second area of vascularity, the vascularity of the second area being less than the vascularity of the first area, the method including the steps of: inserting a device into tissue, the device including a conduit and a filament attached to the conduit, the conduit having a first end, a second end, and a bore therethrough; positioning the first end of the conduit adjacent the outside wall of a torn or damaged area of tissue; positioning the filament through the tissue to secure the conduit and fixate the tissue in a desired position; and securing the filament.

In another form thereof, the present invention provides a method for implanting a medical device in tissue, the method including the steps of: inserting a device into tissue, the device including a plurality of conduits and a filament attached to the conduits, the conduits having a first end, a second end, and a bore therethrough; positioning the first end of each of the conduits adjacent the outside wall of a torn or damaged area of tissue; positioning the filament through the tissue to secure the conduit and fixate the tissue in a desired position; and securing the filament.

BRIEF DESCRIPTION OF THE DRAWINGS

The above-mentioned and other features and advantages of this invention, and the manner of attaining them, will become more apparent and the invention itself will be better understood by reference to the following descriptions of embodiments of the invention taken in conjunction with the accompanying drawings, wherein:

FIG. 3 is a perspective view of the menisci, including a tear in the lateral meniscus and other knee anatomy;

FIG. 4 is a perspective view of the menisci and other knee anatomy following a partial meniscectomy of the lateral meniscus;

FIG. 5 is a partial cross-sectional view along line 5-5 of FIG. 3;

FIG. 6 is a partial cross-sectional view of the lateral meniscus of FIG. 3 including a prior art stent;

FIG. 7 is a plan view of an exemplary embodiment of the conduit of the present invention;

FIG. 7A is a plan view of a conduit according to another exemplary embodiment;

FIG. 7B is a cross-sectional view along line 7B-7B of FIG. 7A;

FIG. 7C is a plan view of a conduit according to another exemplary embodiment;

FIG. 8 is a plan view of a conduit according to another exemplary embodiment;

FIG. 9 is a plan view of a conduit according to another exemplary embodiment;

FIG. 10 is a perspective view of an exemplary embodiment of a device incorporating a conduit according to another exemplary embodiment;

FIG. 11 is a perspective view of the device of FIG. 10 implanted in a meniscus from an interior side of a tear;

FIG. 11A is a perspective view of the device of FIG. 10 implanted in a meniscus from a face of a tear;

FIG. 12 is a cross-sectional view along line 12-12 of FIG. 11;

FIG. 15 is a perspective view of a device according to another exemplary embodiment;

FIG. 16 is a elevational view along line 16-16 of the device of FIG. 15;

FIG. 17 is a perspective view of the device of FIG. 10 implanted in a meniscus and secured according to another exemplary embodiment;

FIG. 19A is a perspective view of the device of FIG. 10 implanted in a meniscus and secured according to another exemplary embodiment;

FIG. 23 is a perspective view of a device according to another exemplary embodiment implanted in a meniscus;

FIG. 24 is a perspective view of a filament and stops used in the device of FIG. 23;

FIG. 25 is a perspective view of an exemplary stop of the device of FIG. 23; and FIG. 26 is a perspective view of a stop according to another exemplary embodiment.

Corresponding reference characters indicate corresponding parts throughout the several views. The exemplifications set out herein illustrate preferred embodiments of the invention and such exemplifications are not to be construed as limiting the scope of the invention in any manner.

DETAILED DESCRIPTION

Figure 1:
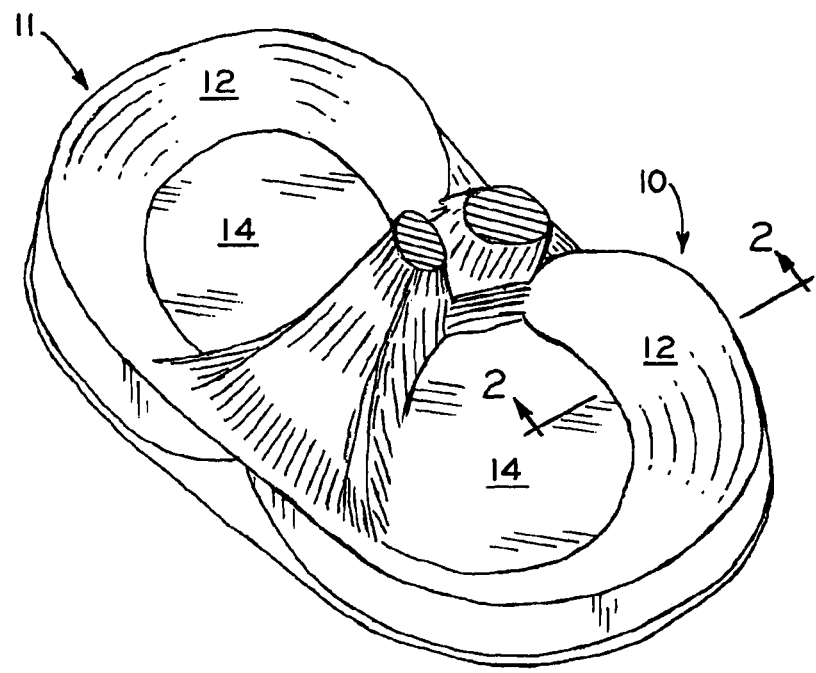
FIG. 1 is a perspective view of the menisci and other knee anatomy.
Figure 2:
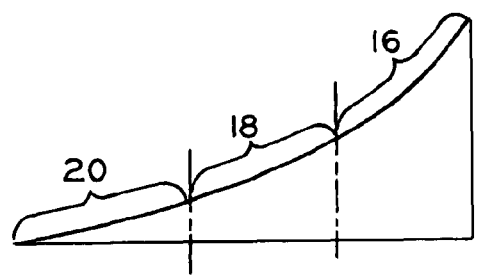
FIG. 2 is a partial cross-sectional view along line 2-2 of FIG. 1.

FIG. 7 shows conduit 30 according to one embodiment of the present invention. The term "conduit", as used herein, means only an elongate body and does not define any other structural features. Conduit 30 includes a first end 32, a second end 34, and through bore 36 extending from first end 32 to second end 34. In one embodiment, bore 36 has a non-circular cross-section. Conduit 30 can be manufactured from any biocompatible material. Conduit 30 has a length from first end 32 to second end 34 as small as 2 mm, 3 mm, or 4 mm and as large as 10 mm, 12 mm, or 15 mm. Additionally, conduit 30 may be coated with biocompatible substances to facilitate tissue regeneration, improve circulation, or achieve any other biologically desirable responses. For example, interior 38 of through bore 36 may be coated with an anti-coagulant to prevent coagulation of blood within through bore 36, thereby promoting the delivery of blood to a torn or damaged tissue area. Alternatively, bore 36 may contain a scaffold material to promote tissue regeneration or to improve healing outcomes.

Conduit 30 may also be made of any porous material which would allow for the transfer of blood from a vascular to an avascular area as a result of physiological processes in the patient's body. Moreover, such a porous construct may be two-piece, shown in FIGS. 7A and 7B, wherein first end 32' of conduit 30' is closed and constructed of a porous material, while the remainder of conduit 30' is made of a substantially solid, biocompatible material. This allows for blood or other fluid to enter second end 34 via bore 36 and exit through the porous material at end 32'. Alternatively, conduit 30 may be constructed entirely of porous material and lack bore 36, as shown in FIG. 7C. Fluid would enter conduit 30 from end 34 and travel, due to the interconnected porosity of the porous material, through conduit 30, exiting at first end 32. The flow of fluid may be directed by altering the material properties of the porous material along the length of conduit 30.

As shown in FIG. 7, conduit 30 further includes a plurality of apertures 42, 44 at end 32 of conduit 30. Apertures 42, 44 extend from interior 38 of through bore 36 to exterior surface 46. Apertures 42, 44 may receive filament 48, as shown in FIG. 10 and described in detail hereinbelow, for securing conduit 30 within tissue and fixating a tear, damaged tissue, or an implant in a desired position. As used herein, the term "filament" is inclusive of single or multiple strands, threads, fibers, strings, wires or sutures. In another exemplary embodiment, apertures 42, 44 are positioned adjacent one another on the same side of conduit 30, i.e., along the axial length of conduit 30, and receive filament 48 in the same manner described in detail herein below. Location of apertures 42, 44 on the same side of conduit 30 provides for eccentric loading of conduit 30 when filament 48 is fully secured, which impedes pull out of conduit 30. Additionally, conduit 30 may include slot 47, shown in FIG. 7, in end 32 of conduit 30 which allow for the exit of blood or other substances therethrough. Slot 47 aids the surgeon in positioning conduit 30 within tissue by eliminating the need for the surgeon to precisely align end 32 of conduit 30 with the plane of a tear, damaged area, or implant to provide blood thereto. As long as the surgeon positions a portion of slot 47 in or adjacent the plane of the tear, damaged area, or implant, blood or other substances will be delivered to the tear, damaged area, or implant. In effect, slot 47 provides an increased length, only a portion of which the surgeon must locate adjacent the tear, damaged tissue, or implant, thereby increasing the likelihood of a successful implantation.

In an exemplary embodiment, end 32 is perforated with a plurality of apertures of sufficient size and spacing to provide a substantially similar benefit as slot 47, described above. In another exemplary embodiment, shown in FIGS. 7A-7B, conduit 30' includes closed end 32' perforated by a plurality of apertures 49 of sufficient size to allow for the dissemination of blood therethrough. In another embodiment, the entire length of conduit 30 is perforated by a plurality of apertures 49 of sufficient size to allow for the dissemination of blood therethrough. Additionally, in another exemplary embodiment, the entire length of conduit 30 is porous, allow the release of fluid along the entire length of conduit 30.

FIGS. 8-10 show conduits 50, 60, 70, respectively, according to additional embodiments of the present invention. Conduits 50, 60, 70 include several features which are identical to the embodiment of FIG. 7 discussed above and identical reference numerals have been used to indicate identical or substantially identical features therebetween. Conduits 50, 60, shown in FIGS. 8 and 9, respectively, include surface features, such as outwardly extending ribs 52 and outwardly extending thread 62, respectively, on external surface 46 of conduits 50, 60. Ribs 52 and threads 62 provide an additional mechanism for fixation of conduits 50, 60 within tissue. As shown in FIG. 10, conduit 70 further includes nose 72. Nose 72 is separated from main body portion 74 via tapering section 76. During implantation, nose 72 facilitates insertion of conduit 70 into the tissue and can be positioned such that nose 72 is in a vascular tissue, such as the synovium, while ribs 52 and/or threads 62 provide fixation. Additionally, nose 72 may itself be tapered to further ease insertion.

As shown in FIG. 10, conduit 70 includes filament 48 attached thereto, forming completed medical device 78. The devices of the present invention are an improvement over the stent disclosed in U.S. patent application Ser. No. 10/558,926 to Schwartz, which is assigned to the assignee of the present invention, the entire disclose of which is incorporated by reference herein. Filament 48 may be manufactured from any flexible, biocompatible material, such as polyglactin, polydioaxanone, surgical gut, nylon, polypropeylyene, polyglycolic acid, polylactic acid, co-polymers, Vicryl®, and Ethibond Excel®. Vicryl® and Ethibond Excel® are registered trademarks of Johnson & Johnson Corporation, One Johnson & Johnson Plaza, New Brunswick, N.J. 08933. Filament 48 and conduit 70 may be preassembled or may be assembled by the surgeon before or during surgery. Filament 48 and conduit 70 may be connected together by inserting a first end (not shown) of filament 48 into interior 38 of through bore 36. The first end of filament 48 is then threaded through aperture 42 and wrapped half-way around exterior surface 46 until the first end reaches aperture 44. In another embodiment, filament 48 is wrapped substantially entirely around exterior surface 46. The first end of filament 48 is then inserted through aperture 44 into interior 38 of through bore 36. First end of filament 48 is then pulled out of through bore 36 through end 32. In another embodiment, exterior surface 46 includes a groove (not shown) on at least a portion of exterior surface 46 transverse to the longitudinal axis of conduit 70. As filament 48 is pulled from end 32 of conduit 70, filament 48 tightens, seating filament 48 within the groove. Once device 78 is assembled, device 78 may be inserted into the meniscus as described in detail hereinbelow.

In another embodiment, the first end of filament 48 is inserted through aperture 42 into interior 38 of through bore 36 and pulled out of through bore 36 through aperture 44. In this embodiment, a portion of filament 48 extends through interior 38 of through bore 36 in a direction transverse to the longitudinal axis of conduit 70. In another embodiment, device 80, as shown in FIGS. 15-16, includes conduit 82 having nose 72, through bore 36, and overmolded end 84. Device 80 include several features which are identical to the embodiment of FIG. 10 discussed above and identical reference numerals have been used to indicate identical or substantially identical features therebetween. As best seen in FIG. 16, overmolded end 84 includes apertures 86, 88 extending from rim 90 of first end 32 toward second end 34 along a portion of conduit 82. Apertures 86, 88 may be formed to be slightly larger than filaments 92, 94 and, during manufacturing, shrink around the ends of filaments 92, 94 to retain the ends therein. Utilizing overmolded end 84 prevents filaments 92, 94 from extending into through bore 36 and provides an uninterrupted path for the flow of blood and other substances therethrough. In another embodiment, a biocompatible adhesive is used to secure the ends of filaments 92, 94 within apertures 86, 88. Once device 80 is assembled, device 80 may be inserted into the meniscus as described in detail hereinbelow.

The method for inserting the devices will now be described in detail with reference to medical device 78, shown in FIG. 10. Device 78 may be inserted into meniscus 10 as shown in FIGS. 11 and 12. In one embodiment, the entire procedure is performed arthroscopically using standard techniques, procedures, and devices. Device 78 is inserted from the interior side of tear at insertion point 100, located between inner rim 102 of meniscus 10 and the interior side of tear 98. In another exemplary embodiment shown in FIG. 11A, the insertion point is the face of tear 98. Device 78 is inserted along a plane substantially parallel to the bottom articulation surface of meniscus 10. While device 78 may be inserted at any angle relative to the bottom articulation surface of meniscus 10, insertion along a plane substantially parallel to the bottom articulation surface provides the optimal purchase for conduit 70. In one embodiment, insertion of device 78 is performed using a compatible insertion tool, such as those disclosed in U.S. patent application Ser. No. 10/558,926 to Schwartz. The insertion tool (not shown) may be inserted into the interior of through bore 36 to retain device 78 thereon and advance device 78 through meniscus 10. In one embodiment, the insertion device is cannulated. The use of a cannulated insertion tool allows for the delivery of biological substances through the insertion device and conduit 70 directly to the torn or damaged area of meniscus 10. In another exemplary embodiment, device 78 is inserted utilizing any technique known technique, including an all-inside technique, inside-out technique, and/or an outside-in technique.

Figure 18:
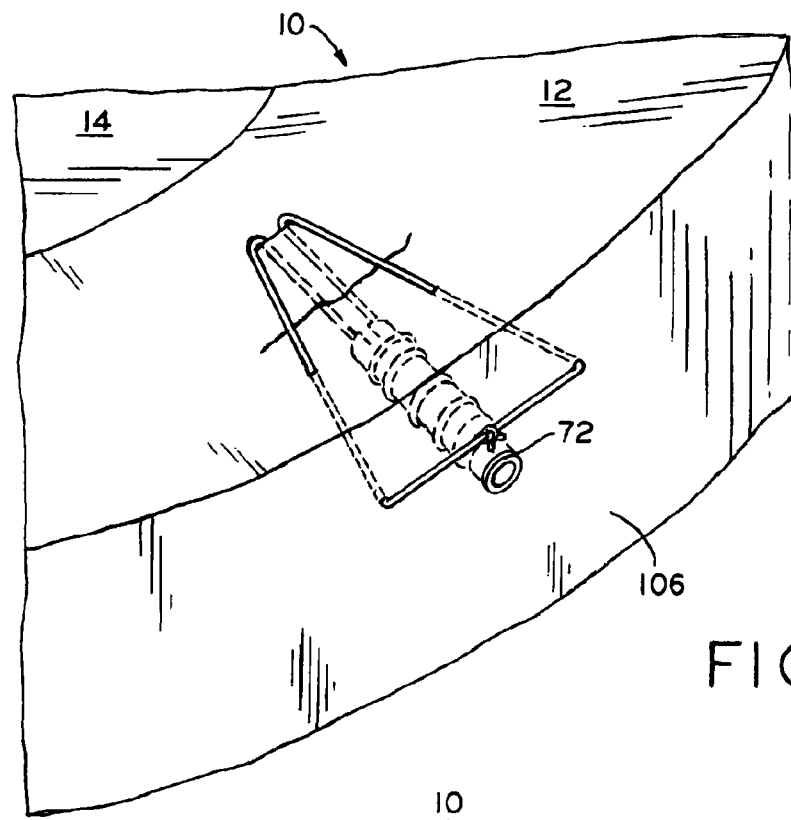
FIG. 18 is a perspective view of the device of FIG. 10 implanted in a meniscus according to another exemplary embodiment.
Figure 21:
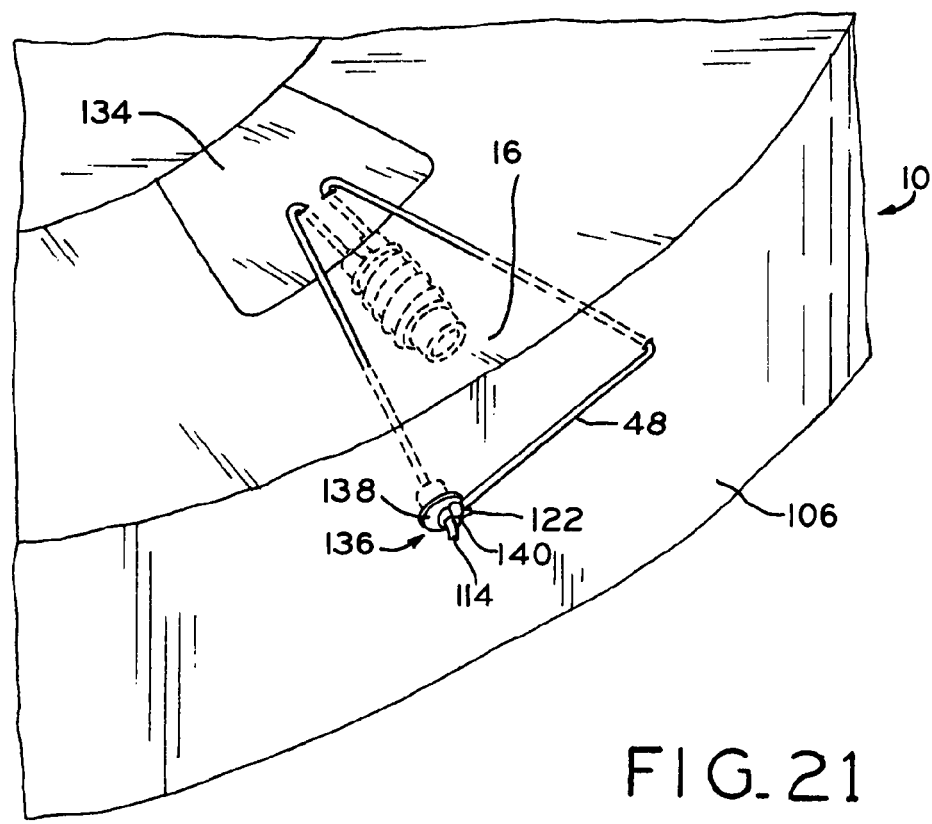
FIG. 21 is a perspective view of the device of FIG. 10 implanted in a meniscus and including a scaffold replacement.

Device 78 is advanced via the insertion tool until end 32 of conduit 70 is substantially aligned with the plane of tear 98, damaged area, or regenerative or replacement meniscus implant 134 (FIG. 21). Additionally, when inserted to align with a damaged area of tissue, the deterioration of the damaged tissue may provide tactile feedback to the surgeon that the outer plane of the damaged area has been encountered. As shown in FIG. 18, conduit 70 may be positioned adjacent a tear, damaged area, or regenerative or replacement meniscus implant 134 with nose 72 extending from outer wall 106 of meniscus 10. In this position, nose 72 extends into the synovium and/or other tissue surrounding the knee joint, which is a highly vascular membrane surrounding the knee. In the same manner as set forth above with reference to red zone 16 of meniscus 10, blood, biological factors, cells, and fluid from the synovium and/or other tissue surrounding the knee joint can be delivered to a torn or damaged area of meniscus 10 via conduit 70.

Referring to FIG. 11, once conduit 70 is positioned, the insertion tool is removed, leaving conduit 70 in position and filament 48 extending from insertion point 100. Ends (not shown) of filament 48 are then looped over tear 98 and inserted in meniscus 10 at second insertion points 103, 104, located between outer wall 106 of meniscus 10 and tear 98 or between inner rim 102 of meniscus 10 and tear 98, using, for example, a needle. The ends of filament 48 are advanced through meniscus 10 at diverging angles until the ends exit outer wall 106 at points 108, 110. The ends of filament 48 are then tightened by pulling the ends away from outer wall 106. In addition to the stitching method set out above, filament 48 can be positioned via any method known to one of ordinary skill in the art, including any horizontal or vertical mattress suture technique.

With filament 48 taut, fixating inner and outer walls of tear 98 in mutual engagement, the ends of filament 48 are secured to one another. Once secured, device 78 is secured and the walls of tear 98 are fixed in their relative positions. In one exemplary embodiment, the ends of filament 48 are secured by tying the ends together to form knot 112, shown in FIG. 11. Excess portions of filament 48 may then be trimmed and discarded.

As shown in FIG. 17, in another exemplary embodiment, first end 114 of filament 48 is secured to a retention device, such as buckle 116, by inserting first end 114 through an aperture in end 118 of buckle 116 and tying end 114 to form knot 120. Second end 122 of filament 48 may then be secured to buckle 116 by inserting second end 122 through opening 128 in buckle 116, looping end 122 around bar 126, through opening 124, and threading end 122 back through opening 128. In this manner, filament 48 is looped back onto itself and retained by friction within buckle 116. For large tears or damaged areas, multiple devices may be implanted in accordance with the method described hereinabove.

Figure 19:
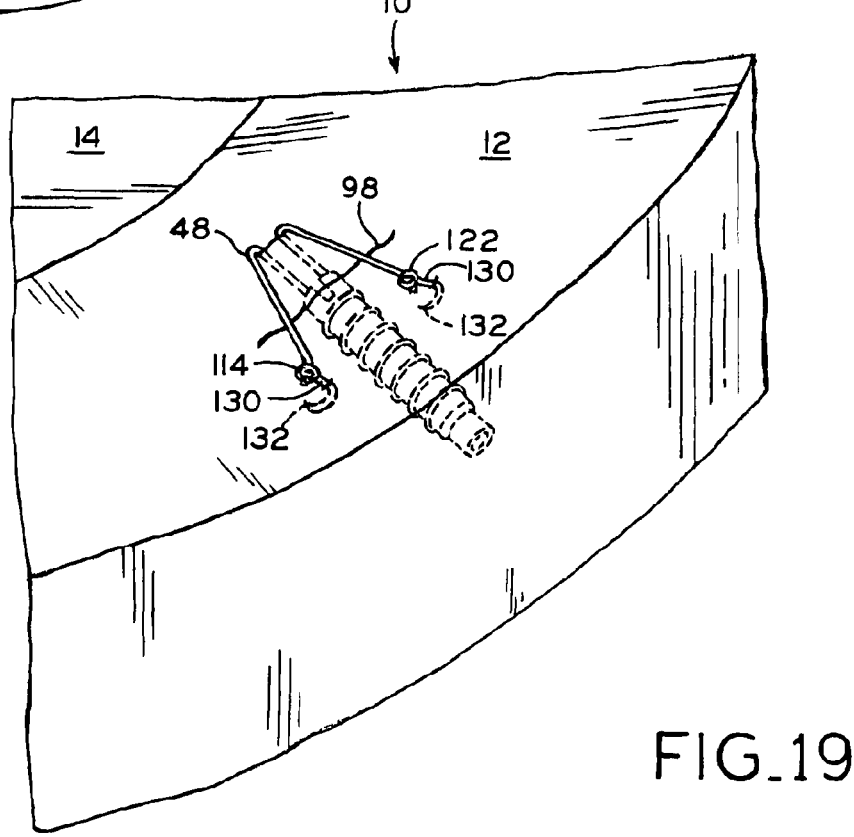
FIG. 19 is a perspective view of the device of FIG. 10 implanted in a meniscus and secured according to another exemplary embodiment.

As shown in FIG. 19, in another exemplary embodiment, first end 114 and second end 122 of filament 48 are secured, via knots for example, to hooks 130. Hooks 130 are curved and terminate at sharpened tips 132. At any time during the procedure, tips 132 are inserted through the upper articulation surface 12 of meniscus 10. Once conduit 70 is properly positioned and hooks 130 attached to meniscus 10 via tips 132, filament 48 acts to fixate tear 98 and secure conduit 70 in position, as described hereinabove.

In another exemplary embodiment, shown in FIG. 19A, first end 114 and second end 122 of filament 48 are pulled tight through top articulating surface 12 of meniscus 10. Knot 115 is tied using first end 114 and knot 117 is tied using second end 122 to secure the walls of tear 98 in mutual engagement. Due to the physical properties of meniscus 10, knots 115, 117 will sink into top articulating surface 12, preventing any damage to or pain in the patient's knee. Similarly, any other securement method or device disclosed herein may potentially be used atop top articulating surface 12 to secure ends 114, 122 of filament 48 together and fixate tissue in the desired position.

Figure 20:
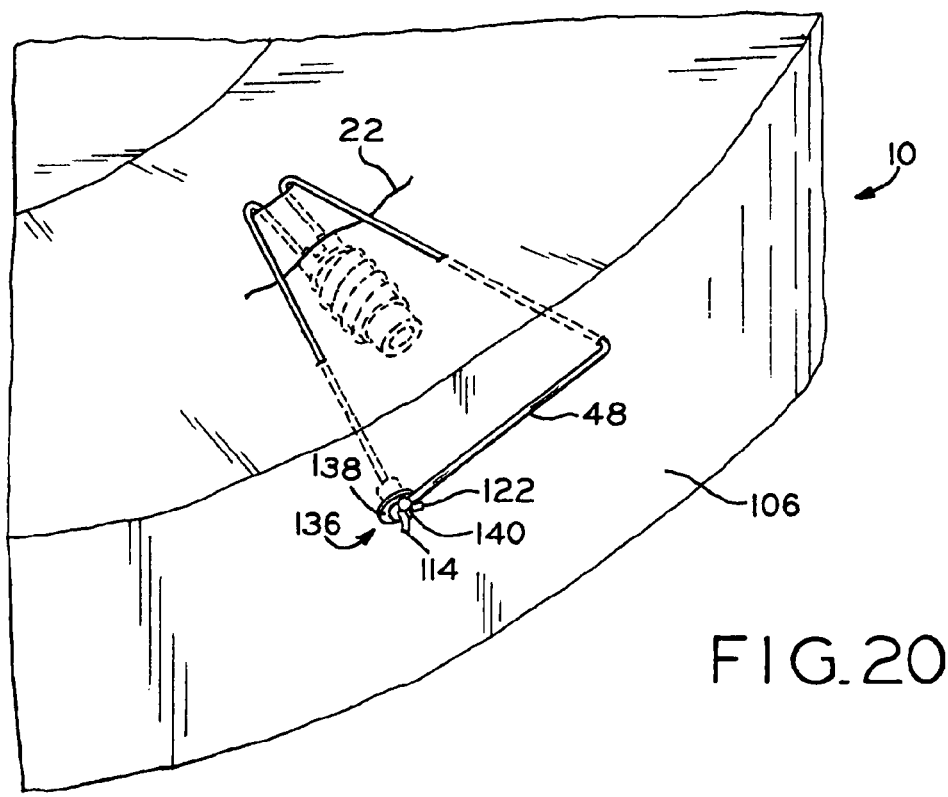
FIG. 20 is a perspective view of the device of FIG. 10 implanted in a meniscus and secured according to another exemplary embodiment.

Additionally, in another exemplary embodiment shown in FIGS. 20-21, conduit 70 is positioned within meniscus 10 in a similar manner as described hereinabove. To secure conduit 70 in position within meniscus 10 and fixate tear 22 or regenerative or replacement meniscus implant 134, shown in FIG. 21, slide 136 is used. Slide 136 has a body with a bore extending therethrough and flange 138 projecting from an end of the body of slide 136. First end 114 of filament 48 is threaded through the bore of slide 136 toward flange 138. Second end 122 of filament 48 is then secured to first end 114 of filament 48 via slipknot 140. By pulling first end 114 of filament 48 away from outer wall 106 of meniscus 10, slipknot 140 moves toward outer wall 106 and pushes slide 136 into meniscus 10. Once filament 48 is taught, flange 138 will contact outer wall 106 of meniscus 10, preventing slipknot 140 from sliding further. Slipknot 140 can then be tightened to secure ends 114, 122 of filament 48 together. Once secured, ends 114, 122 of filament 48 may be trimmed and the removed portion discarded.

While the devices of the present invention may be implanted as an alternative to a meniscectomy, the devices may also be implanted in native meniscus tissue or a regenerative or replacement meniscus implant following a meniscectomy to encourage and/or promote tissue regeneration and, when a regenerative or replacement meniscus implant is used, the device may further fixate the implant to the natural meniscus tissue, as shown in FIG. 21. As shown in FIG. 21, regenerative or replacement meniscus implant 134 is fixated via filament 48 in position against natural meniscus 10. Implant 134 further receives blood, biological factors, cells, and other fluids from the red zone 16 of meniscus or, in another embodiment shown in FIG. 18, from the synovium via conduit 70.

Figure 13:
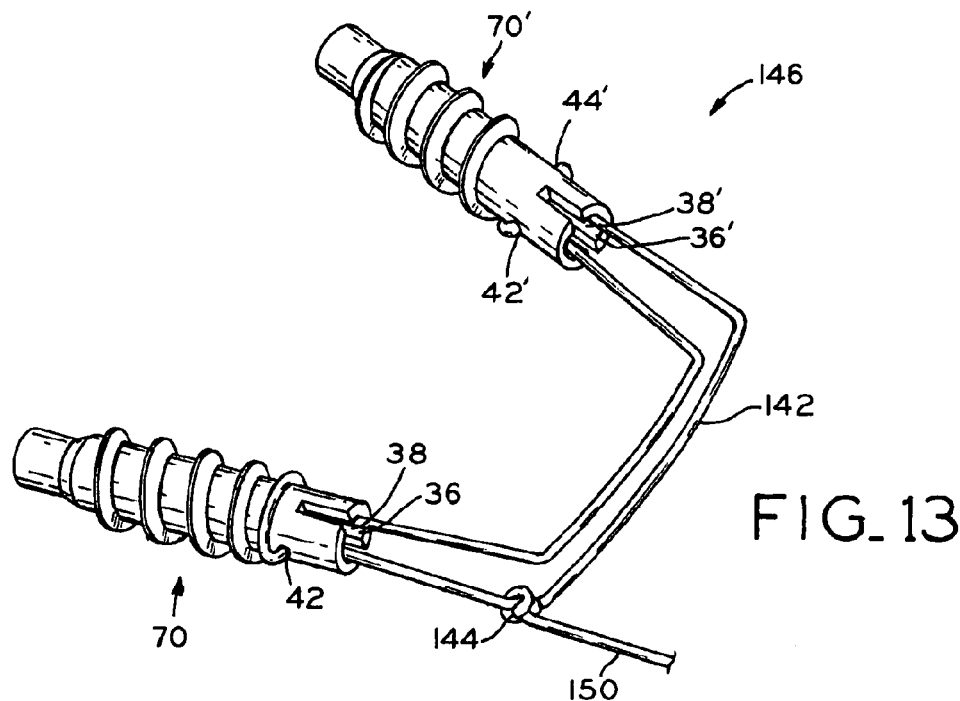
FIG. 13 is a perspective view of a device according to another exemplary embodiment.
Figure 14:
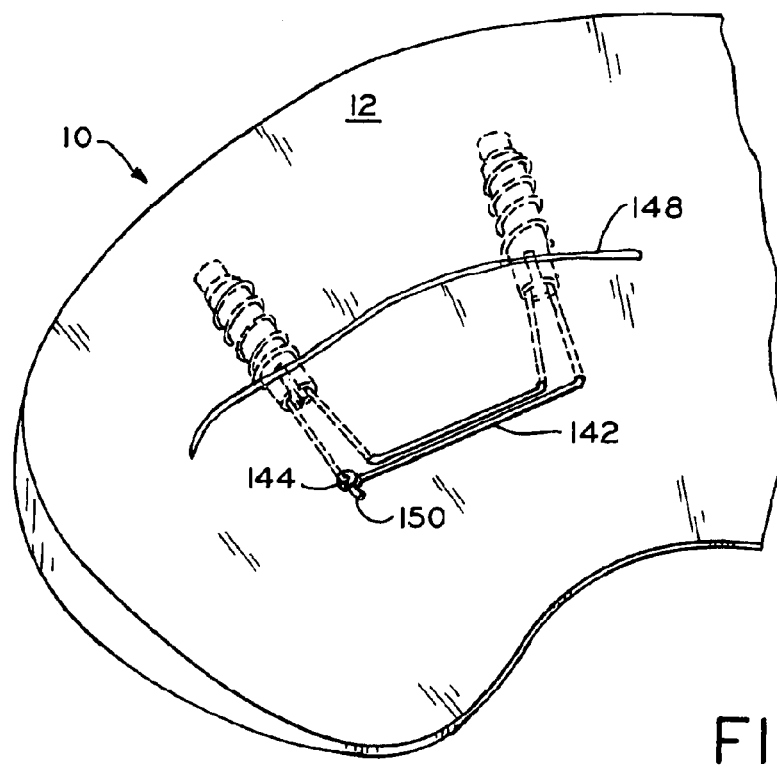
FIG. 14 is a perspective view of the device of FIG. 13 implanted in a meniscus.

As shown in FIG. 13-14, two conduits 70, 70' are connected together via filament 142. In connecting the conduits, a first end of filament 142 is inserted through interior 38 of through bore 36 of conduit 70, pulled from aperture 42, and wrapped half way around conduit 70. The end is then inserted through aperture 44, shown in hidden lines in FIG. 10, and pulled from interior 38 of through bore 36, as discussed in detail hereinabove. Filament 142 is then inserted through interior 38' of through bore 36' of conduit 70', pulled from aperture 42', and wrapped half way around conduit 70'. The end is then inserted through aperture 44' and pulled from interior 38' of through bore 36', as discussed in detail hereinabove. The ends of filament 142 are then connected together via slipknot 144, forming device 146. While two conduits are depicted in FIG. 13, any number of conduits needed to facilitate tissue regeneration and healing may be connected together. Generally, as the size of the tear or damaged area increases, the number of conduits needed to facilitate tissue regeneration and healing will correspondingly increase.

By using multiple conduits, blood and/or other substances can be delivered to multiple points along the plane of a tear or damaged area of tissue and fixated by the tightening of only a single filament. The insertion of device 146 will now be described in detail. Conduits 70, 70' are inserted individually relative to tear 148 using the same procedure discussed hereinabove with respect to conduit 70 and tear 98. Once each conduit 70, 70' is properly inserted, as shown in FIG. 14, filament 142 remains partially exposed along top articulating surface 12 of meniscus 10. Filament 142 is then tightened, by pulling end 150 of filament 142 away from top articulating surface 12 until the inner and outer walls of tear 148 are in mutual engagement. The interference of top articulating surface 12 of meniscus 10 with the tightening of filament 142 secures conduits 70, 70' in their desired positions.

In one exemplary embodiment, a knot (not shown) is used to fix filament 142, and correspondingly secure device 146, in position. In one exemplary embodiment, slipknot 144 is used to retain filament 142 in the tightened position. To tighten filament 142, end 150 is pulled away from top articulating surface 12 of meniscus 10 and, at the same time, slipknot 144 slides downwardly toward top articulating surface 12. Once slipknot 144 is tightened, excess filament 142 can be trimmed and discarded. Due to the resilient nature of fibrocartilage tissue, filament 142 and slipknot 144 will become integrated with meniscus preventing any adverse effects, such pain or discomfort during articulation of the condyles of the femur against top articulation surface 12 and filament 142. In one embodiment, a series of devices 78, shown in FIG. 10, may be utilized with a single tear. Each device 78 can then be fixated in the manner discussed hereinabove providing additional tension on tear 98, shown in FIG. 11, and placing knot 112 outside of the contact area of meniscus 10 and against outer wall 106.

Referring to FIGS. 23-25, another exemplary embodiment utilizing conduits 70, 70' is shown. In this embodiment, conduits 70, 70' are inserted through tear 170 individually and prior to attachment of filament 172. Specifically, conduits 70, 70' are inserted through the one of the walls forming tear 170 closest to outer wall 106 of meniscus 10. In one exemplary embodiment, noses 72, 72' of conduits 70, 70' may extend from outer wall 106 of meniscus 10, as described in detail above. Once conduits 70, 70' are inserted into meniscus 10, filament 172 and stops 174 may be secured to conduits 70, 70'. While described and depicted herein as utilizing two conduits 70, 70' and two stops 174, any number of conduits may be used in conjunction with any number of stops to provide the desired fixation of tear 170.

Referring to FIGS. 24-25, stop 174 include apertures 176, 178 extending therethrough. As shown in FIG. 25, stop 174 is formed as an elongate rod. By forming stops 174 as elongate rods, stops 174 allow for fluid to pass through bores 36, 36' (FIG. 13) of conduits 70, 70'. However, stops 174 may be formed in any other geometric shape, such as square rods or circular discs. For example, referring to FIG. 26, stop 174' is shown in the form of a circular disc have apertures 176', 178' extending therethrough. Stop 174' may replace stop 174 and may be utilized in the same manner as described herein with reference to stop 174. In connecting filament 172 to stops 174, first end 180 of filament 172 is threaded through aperture 176 of stop 174. First end 180 is then threaded through aperture 178 of stop 174. A second stop 174 is then provided and connected to filament 172 in a similar manner. First end 180 of filament 172 is then used to tie slipknot 182 on filament 172 and the remainder of first end 180 is then trimmed.

Once stops 174 are attached to filament 172, as shown in FIG. 24, filament 172 and stops 174 are inserted into meniscus 10. Specifically, longitudinal axes 184 (FIG. 25) of stops 174 are aligned with bores 36, 36' of conduits 70, 70' and inserted at insertion points 190. Since stops 174 have an outer diameter that is less then the inner diameter of bores 36, 36', once aligned, stops 174 may be inserted through bores 36, 36', respectively, and then through outer wall 106 of meniscus 10. Stops 174 may be inserted in unison or, alternatively, may be inserted individually. For example, one of stops 174 may be inserted through bore 36 of conduit 70 and outer wall 106. Then, the other of stops 174 may be inserted through bore 36' of conduit 70' and outer wall 106. Once inserted as described in detail above, end 186 and a portion of filament 172 extends from articulating surface 12 of meniscus 10. End 186 of filament 172 may then be pulled away from articulating surface 12. As end 186 is pulled away from articulating surface 12 of meniscus 10, slipknot 182 of filament 172 tightens as filament 172 slides through apertures 176, 178 of stops 174 and bores 36, 36' of conduits 70, 70'. In this manner, pulling on end 186 of filament 172 allows for the tightening of the entire construct to fixate the opposing sides of tear 170 adjacent one another and fixate conduits 70, 70' in their desired positions. Once tightened, end 186 of filament 172 may be trimmed to remove any excess material.

Figure 22:
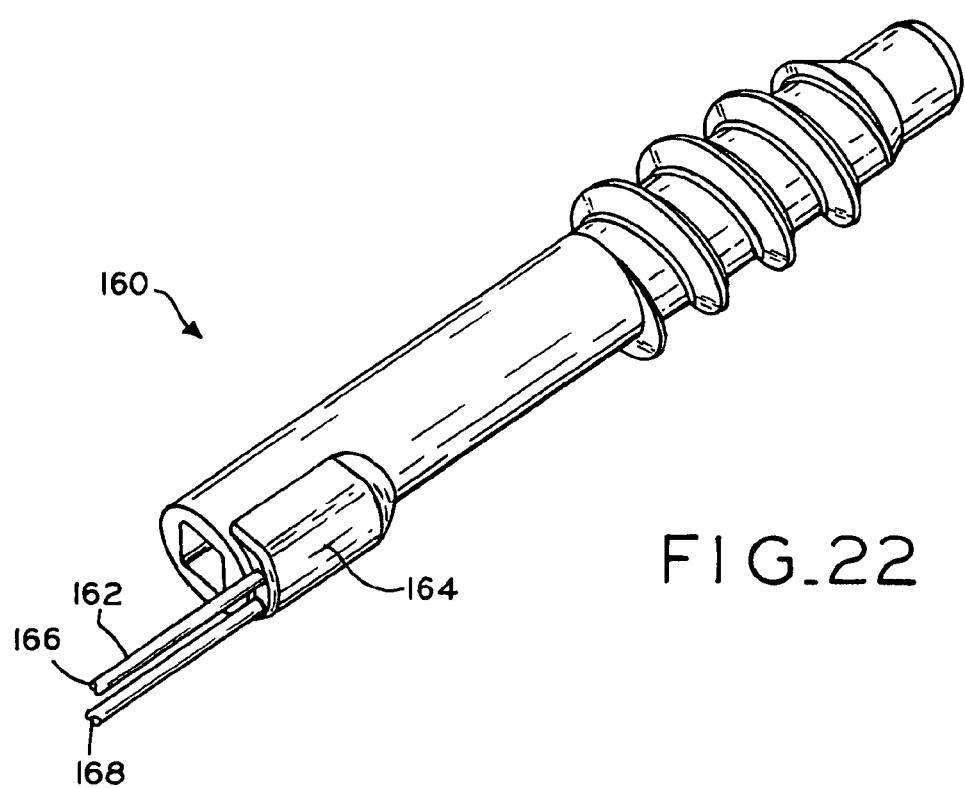
FIG. 22 is a perspective view of a device according to another exemplary embodiment.

In another exemplary embodiment, conduit 160, shown in FIG. 22, includes filament 162 secured through apertures in projection 164. Projection 164 may be overmolded, as described in detail above, or may allow for sliding movement of filament 162 within projection 164. If sliding movement of filament 162 is allowed, end 166 of filament 162 could be pulled away from projection 164 drawing end 168 toward projection 164. In another embodiment, projection 164 is replaced by apertures located adjacent one another on the same side of conduit 160, i.e., along the axial length of conduit 160. These apertures accept filament 162 in the same manner as apertures 42, 44, described in detail above with reference to FIGS. 7-10. The use of either projection 164 or the apertures located on the same side of conduit 160 provides for eccentric loading of conduit 160 when filament 162 finally secured, which impedes pull out of conduit 160.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A method for repairing torn tissue of a patient, the tissue having a first area of vascularity and a second area of vascularity, the vascularity of the second area being less than the vascularity of the first area, the method comprising:
   simultaneously inserting a conduit having a longitudinal bore and a portion of a filament disposed within the longitudinal bore through an aperture defined by a tear in the torn tissue, through an insertion point at a face of the tear, and into the tissue, the conduit having a first end and a second end;
   positioning the conduit such that the first end is adjacent to the tear;
   fixating the tissue with the filament; and
   securing the filament.

2. The method of claim 1 wherein the tear is in the second area of vascularity, and wherein positioning the conduit further includes positioning the second end of the conduit within the first area of vascularity.

3. The method of claim 1 wherein inserting the conduit includes utilizing an all-inside technique.

4. The method of claim 1 wherein inserting the conduit includes utilizing an inside-out technique.

5. The method of claim 1 wherein inserting the conduit includes utilizing an outside-in technique.

6. The method of claim 1 further comprising attaching a stop to the filament, and inserting the stop through the longitudinal bore of the conduit.

7. The method of claim 6 wherein the stop includes at least one aperture, and wherein attaching the stop to the filament includes threading the filament through the at least one aperture.

8. The method of claim 6 further comprising positioning the stop through an outer wall of the tissue.

9. The method of claim 6 wherein the stop is selected from the group consisting of a cylindrical rod, a square rod, and a circular disc.

10. The method of claim 1 wherein the conduit further includes a surface feature selected from the group consisting of ribs and threading, and wherein positioning the conduit further includes fixating the conduit within the tissue such that the surface feature engages the tissue.

11. The method of claim 1 wherein the filament includes a first end and a second end, and securing the filament includes forming a slipknot with the second end, passing the first end through the slipknot, and tightening the slipknot.

12. A method for repairing torn tissue of a patient, the tissue having a first area of vascularity and a second area of vascularity, the vascularity of the second area being less than the vascularity of the first area, the method comprising:
   simultaneously inserting a first conduit having a longitudinal bore and a first portion of a filament disposed within the longitudinal bore through an aperture defined by a tear in the torn tissue, through an insertion point at a face of the tear, and into the tissue, the first conduit having a first end and a second end;
   simultaneously inserting a second conduit having a longitudinal bore and a second portion of the filament disposed within the longitudinal bore of the second conduit through the aperture defined by the tear, through an insertion point at the face of the tear, and into the tissue, the second conduit having a first end and a second end;
   positioning each conduit such that its first end is adjacent to the tear;
   fixating the tissue with the filament; and
   securing the filament.

13. The method of claim 12 wherein the tear of the tissue is in the second area of vascularity, and wherein positioning each conduit further includes positioning its second end within the first area of vascularity.

14. The method of claim 12 further comprising attaching at least one stop to the filament, and wherein simultaneously inserting the first conduit and the first portion of the filament includes inserting the at least one stop through the longitudinal bore of the first conduit.

15. The method of claim 14 wherein inserting the at least one stop includes inserting one stop through each of the longitudinal bores.

16. The method of claim 14 wherein the at least one stop includes at least one aperture, and wherein attaching the stop to the filament includes threading the filament through the at least one aperture.

17. The method of claim 14 further comprising positioning the at least one stop through an outer wall of the tissue.

18. The method of claim 12 wherein the filament includes a first end and a second end, and securing the filament includes forming a slipknot with the second end, passing the first end through the slipknot, and tightening the slipknot.

* * * * *